United States Patent [19]

Thornton

[11] Patent Number: 5,755,219
[45] Date of Patent: May 26, 1998

[54] DEVICE FOR IMPROVING BREATHING

[76] Inventor: W. Keith Thornton, 5524 Edlen, Dallas, Tex. 75220

[21] Appl. No.: 645,673

[22] Filed: May 14, 1996

Related U.S. Application Data

[63] Continuation-in-part of Ser. No. 253,949, Jun. 3, 1994, Pat. No. 5,537,994.

[51] Int. Cl.⁶ ................................................. A61M 21/00
[52] U.S. Cl. .......................... 128/201.18; 128/204.18; 128/201.26; 128/848
[58] Field of Search .................... 128/200.24, 201.18, 128/201.26, 204.18, 206.29, 848, 859, 861, 862, 869

[56] References Cited

U.S. PATENT DOCUMENTS

| | | | |
|---|---|---|---|
| Re. 33,442 | 11/1990 | George | 128/860 |
| 746,869 | 12/1903 | Moulton | 128/848 |
| 774,446 | 11/1904 | Moulton | 128/848 |
| 885,196 | 4/1908 | Steil | 128/848 |
| 893,213 | 7/1908 | Whiteway | |
| 1,076,534 | 10/1913 | Wallen | 433/44 |
| 1,146,264 | 7/1915 | Kelly | 602/6 |
| 1,483,694 | 2/1924 | Stukey | 128/859 |
| 1,649,664 | 11/1927 | Carter | 33/514 |
| 1,674,336 | 6/1928 | King | 128/848 |
| 2,171,695 | 9/1939 | Harper | 433/42 |
| 2,178,128 | 10/1939 | Waite | 128/136 |
| 2,383,649 | 8/1945 | Heidbrink | 128/142 |
| 2,424,533 | 7/1947 | Faires | 128/136 |
| 2,521,039 | 9/1950 | Carpenter | 128/136 |
| 2,521,084 | 9/1950 | Oberto | 128/141 |
| 2,531,222 | 11/1950 | Kesling | 32/14 |
| 2,574,623 | 11/1951 | Clyde | 128/136 |
| 2,590,118 | 3/1952 | Oddo, Jr. | 128/136 |
| 2,627,268 | 2/1953 | Leppich | 128/136 |
| 2,833,278 | 5/1958 | Ross | 128/136 |
| 2,867,212 | 1/1959 | Nunn, Jr. | 128/136 |
| 2,882,893 | 4/1959 | Godfroy | 128/136 |

(List continued on next page.)

FOREIGN PATENT DOCUMENTS

| | | | |
|---|---|---|---|
| 0312368 | 4/1989 | European Pat. Off. | A61F 5/56 |
| 0359135 | 3/1990 | European Pat. Off. | A63B 71/10 |
| 156627 | 12/1904 | Germany . | |
| 2320501 | 11/1974 | Germany | A61F 5/56 |
| 3707952 | 9/1988 | Germany . | |
| 1569129 | 6/1980 | United Kingdom | A61F 5/56 |

OTHER PUBLICATIONS

Great Lakes Orthodontics, Ltd., Nocturnal Airway Patency Appliance ™ (NAPA) Brochure, undated, 2 pages.

George, "Treatment of Snoring and Obstructive Sleep Apnea with a Dental Device," *General Denistry*, Jul.–Aug. 1993, 5 pages.

Schmidt–Nowara, et al., "Oral Appliances for the Treatment of Snoring and Obstructive Sleep Apnea: A Review," *Sleep*, vol. 18, No. 16, 1995, 10 pages.

2–piece dental device manufactured by Currie–Gibson Dental Laboratory, Inc. prior to Apr. 13, 1993.

*Mayo Clinic Health Letter*, vol. 13, No. 7, "Snoring," Jul. 1995.

Photocopies of 2–piece dental device (date and source unknown).

Farrar & McCarty, "A Clinical Outline of Temporomandibular Joint Diagnosis and Treatment," Normandie Study Group for TMJ Dysfunction, 1993, 3 pages.

Professional Positioners brochure "Dedicated to excellence", 4 pages (date unknown).

*Primary Examiner*—Aaron J. Lewis
*Assistant Examiner*—V. Srivastava
*Attorney, Agent, or Firm*—Baker & Botts, L.L.P.

[57] ABSTRACT

A device for improving breathing (10) includes an upper arch (12) adapted to receive at least some of a user's upper teeth and a lower arch (14) adapted to receive at least some of the user's lower teeth. A tensile member (24) is coupled to the upper arch (12) and the lower arch (14), and exerts a tensile force upon the lower arch (14). The device (10) adjustably positions the lower arch (14) forwardly, relative to the upper arch (12), using the tensile force.

20 Claims, 2 Drawing Sheets

U.S. PATENT DOCUMENTS

| | | | |
|---|---|---|---|
| 3,107,668 | 10/1963 | Thompson | 128/136 |
| 3,124,129 | 3/1964 | Grossberg | 128/136 |
| 3,132,647 | 5/1964 | Corniello | 128/136 |
| 3,219,033 | 11/1965 | Wallshein | 128/136 |
| 3,277,892 | 10/1966 | Tepper | 128/172.1 |
| 3,312,216 | 4/1967 | Wallshein | 128/136 |
| 3,321,832 | 5/1967 | Weisberg | 32/32 |
| 3,434,470 | 3/1969 | Strickland | 128/136 |
| 3,457,916 | 7/1969 | Wolicki | 128/136 |
| 3,513,838 | 5/1970 | Foderick et al. | 128/861 |
| 3,522,805 | 8/1970 | Wallshein | 128/136 |
| 3,854,208 | 12/1974 | Arant | 32/19 |
| 3,864,832 | 2/1975 | Carlson et al. | 128/136 |
| 3,871,370 | 3/1975 | McDonald | 128/136 |
| 3,884,226 | 5/1975 | Tepper | 128/136 |
| 4,016,650 | 4/1977 | Leusner et al. | 32/17 |
| 4,026,024 | 5/1977 | Tradowsky | 32/19 |
| 4,114,614 | 9/1978 | Kesling | 128/136 |
| 4,169,473 | 10/1979 | Samelson | 128/136 |
| 4,182,312 | 1/1980 | Mushabac | 433/68 |
| 4,227,877 | 10/1980 | Tureaud et al. | 433/37 |
| 4,289,127 | 9/1981 | Nelson | 128/207.14 |
| 4,304,227 | 12/1981 | Samelson | 128/136 |
| 4,376,628 | 3/1983 | Aardse | 433/80 |
| 4,382,783 | 5/1983 | Rosenberg | 433/19 |
| 4,433,956 | 2/1984 | Witzig | 433/7 |
| 4,439,147 | 3/1984 | Magill et al. | 433/3 |
| 4,439,149 | 3/1984 | Devincenzo | 433/6 |
| 4,470,413 | 9/1984 | Warncke | 128/201.18 |
| 4,495,945 | 1/1985 | Leigner | 128/200.26 |
| 4,505,672 | 3/1985 | Kurz | 433/6 |
| 4,553,549 | 11/1985 | Pope et al. | 128/421 |
| 4,568,280 | 2/1986 | Ahlin | 433/6 |
| 4,569,342 | 2/1986 | von Nostitz | 128/136 |
| 4,593,686 | 6/1986 | Lloyd et al. | 128/136 |
| 4,602,905 | 7/1986 | O'Keefe, III | 433/41 |
| 4,639,220 | 1/1987 | Nara et al. | 433/69 |
| 4,655,213 | 4/1987 | Rapoport et al. | 128/205.25 |
| 4,669,459 | 6/1987 | Spiewak et al. | 128/136 |
| 4,676,240 | 6/1987 | Gardy | 128/207.14 |
| 4,715,368 | 12/1987 | George | 128/136 |
| 4,773,853 | 9/1988 | Kussick | 433/6 |
| 4,799,500 | 1/1989 | Newburg | 128/859 |
| 4,862,903 | 9/1989 | Campbell | 128/861 |
| 4,901,737 | 2/1990 | Toone | 128/848 |
| 4,919,128 | 4/1990 | Kopala et al. | 128/207.18 |
| 4,932,867 | 6/1990 | Ueno | 433/69 |
| 4,955,393 | 9/1990 | Adell | 128/859 |
| 5,003,994 | 4/1991 | Cook | 128/848 |
| 5,018,533 | 5/1991 | Hawkins | 128/848 |
| 5,028,232 | 7/1991 | Snow | 433/24 |
| 5,042,506 | 8/1991 | Liberati | 128/848 |
| 5,046,512 | 9/1991 | Murchie | 128/848 |
| 5,052,409 | 10/1991 | Tepper | 128/859 |
| 5,056,534 | 10/1991 | Wright | 128/848 |
| 5,078,600 | 1/1992 | Austin | 433/73 |
| 5,092,346 | 3/1992 | Hays et al. | 128/848 |
| 5,103,838 | 4/1992 | Yousif | 128/859 |
| 5,117,816 | 6/1992 | Shapiro et al. | 128/200.24 |
| 5,154,184 | 10/1992 | Alvarez | 128/848 |
| 5,154,609 | 10/1992 | George | 433/68 |
| 5,183,057 | 2/1993 | Syrop et al. | 128/845 |
| 5,188,529 | 2/1993 | Luth | 433/68 |
| 5,267,862 | 12/1993 | Parker | 433/215 |
| 5,277,202 | 1/1994 | Hays | 128/848 |
| 5,284,161 | 2/1994 | Karell | 128/848 |
| 5,313,960 | 5/1994 | Tomasi | 128/848 |
| 5,316,020 | 5/1994 | Truffer | 128/848 |
| 5,365,945 | 11/1994 | Halstrom | 128/848 |
| 5,373,859 | 12/1994 | Forney | 128/846 |
| 5,409,017 | 4/1995 | Lowe | 128/848 |
| 5,427,117 | 6/1995 | Thornton | 128/848 |
| 5,537,994 | 7/1996 | Thornton | 128/204.18 |
| 5,566,683 | 10/1996 | Thornton | 128/848 |

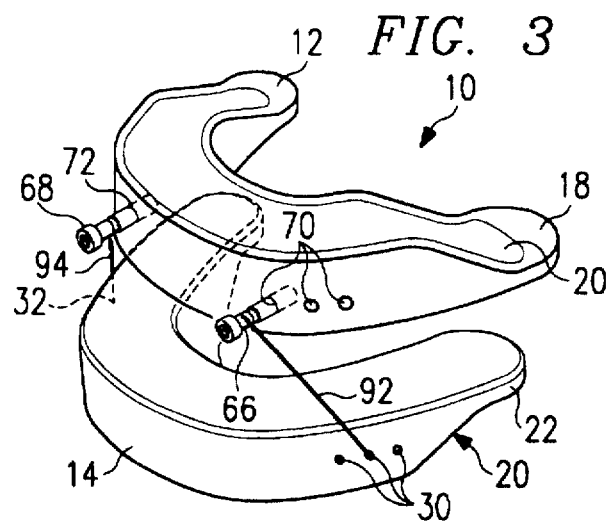
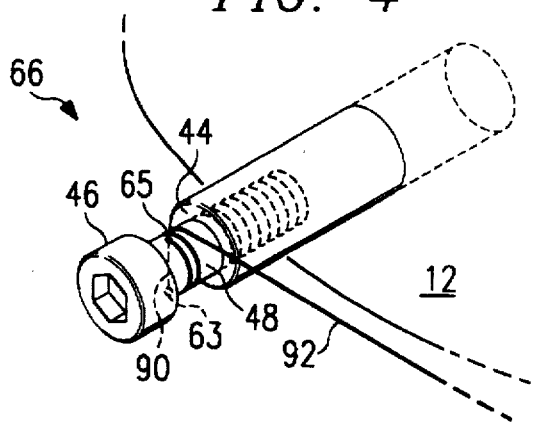
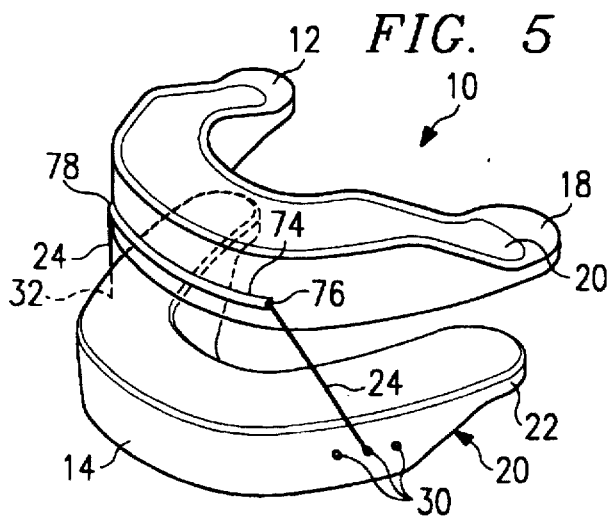

DEVICE FOR IMPROVING BREATHING

CROSS-REFERENCE TO RELATED APPLICATIONS

This application is a continuation in part of U.S. application Ser. No. 08/253,949, filed Jun. 3, 1994, by W. Keith Thornton now U.S. Pat. No. 5,557,994 and entitled "Combination Face Mask And Dental Device For Improved Breathing During Sleep."

In addition, this application is related to U.S. application Ser. No. 08/582,526, filed Jan. 3, 1996, by W. Keith Thornton now abandoned and entitled "Device For Improving Breathing," which is a continuation in part of U.S. application Ser. No. 08/253,949, now U.S. Pat. No. 5,537,994 filed Jun. 3, 1994, by W. Keith Thornton and entitled "Combination Face Mask And Dental Device For Improved Breathing During Sleep." This application is also related to U.S. application Ser. No. 08/501,437, filed Jul. 12, 1995, by W. Keith Thornton and Andrew O. Jamieson now U.S. Pat. No. 5,678,567 and entitled "Apparatus For Adjusting A Dental Device," which is a continuation of U.S. application Ser. No. 08/435,277, filed May 5, 1995, now abandoned by W. Keith Thornton and Andrew O. Jamieson and entitled "Method And Apparatus For Adjusting A Dental Device," which is a continuation application of abandoned U.S. application Ser. No. 08/218,719, filed Mar. 25, 1994, by W. Keith Thornton and Andrew O. Jamieson and entitled "Method And Apparatus For Adjusting A Dental Device."

TECHNICAL FIELD OF THE INVENTION

This invention relates generally to medical devices, and more particularly to a device for improving breathing.

BACKGROUND OF THE INVENTION

Many people experience breathing problems. These problems may result in difficulty sleeping, in snoring, or in more serious conditions such as sleep apnea.

One treatment for breathing disorders involves the use of devices inserted into a user's mouth for extending the user's lower jaw forward. These devices may open the user's breathing passageway more fully and thereby allow the user to breathe more easily through the nose and mouth. Although these devices may treat some breathing problems, these devices may not adequately treat more serious conditions such as sleep apnea. Furthermore, these devices often lack the customizability and adjustability necessary to serve a variety of users and treatment requirements.

SUMMARY OF THE INVENTION

In accordance with the present invention, the disadvantages and problems associated with devices for improving breathing have been substantially reduced or eliminated.

In accordance with one embodiment of the present invention, a device for improving breathing includes an upper arch adapted to receive at least some of a user's upper teeth and a lower arch adapted to receive at least some of the user's lower teeth. A tensile member is coupled to the upper arch and the lower arch, and exerts a tensile force upon the lower arch. The device adjustably positions the lower arch forwardly, relative to the upper arch, using the tensile force. In another embodiment, the device includes an upper arch having a channel operable to receive the tensile member. In yet another embodiment, a plurality of tensile members adjustably position the lower arch forwardly, relative to the upper arch.

Important technical advantages of the present invention include providing a device for improving breathing that is readily customizable by the user or a clinical professional. Therefore, the device may be constructed so as to fit the user's mouth more securely and to more effectively treat the user's particular breathing disorder. Furthermore, because the device is customizable by the user as well as by a clinical professional, the device and associated treatment may be less expensive than would otherwise be possible.

Another important technical advantage of the present invention is the fact that it adjustably positions the user's jaw forwardly, relative to the upper jaw, while permitting the lower jaw to move laterally. Therefore, the user's comfort may be increased without reducing the effectiveness of the device. In particular embodiments, forward adjustment of the lower jaw is accomplished using one or more tensile members that may be adjusted independently or together. As a result, the present invention provides increased adaptability in addition to more effectively treating serious breathing disorders such as sleep apnea.

BRIEF DESCRIPTION OF THE DRAWINGS

For a more complete understanding of the present invention and for further features and advantages thereof, reference is now made to the following description taken in conjunction with the accompanying drawings, in which:

FIG. 3 illustrates an alternative device for improving breathing;

FIG. 4 illustrates an exploded view of an alternative adjuster; and

FIG. 5 illustrates another alternative device for improving breathing.

DETAILED DESCRIPTION OF THE INVENTION

Figure 1:
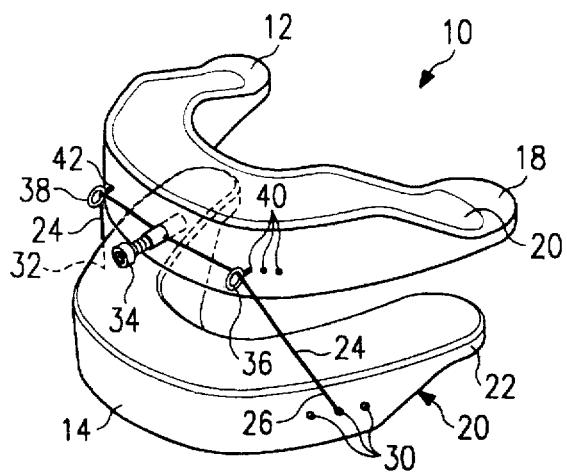
FIG. 1 illustrates a device for improving breathing.

FIG. 1 illustrates a device for improving breathing, indicated generally at 10, that includes an upper arch 12 adapted to receive at least some of a user's upper teeth and a lower arch 14 adapted to receive at least some of the user's lower teeth. When device 10 is in use, upper arch 12 and lower arch 14 are inserted into the user's mouth.

Upper and lower arches 12 and 14 include trays 18 and 22, respectively. Trays 18 and 22 may be formed from any material suitable for dental uses, for example, methyl methacrylate or a polycarbonate resin thermoplastic such as that sold under the Registered Trademark Lexan. Such materials are known to those familiar with dental devices, and other suitable materials may be used to form trays 18 and 22 without departing from the intended scope of the present invention.

Trays 18 and 22 are adapted to receive a deformable material 20 in which molds of at least some of the user's upper and lower teeth, respectively, may be formed. Deformable material 20 may be formed from any suitable material, for example, a polyvinyl acetate such as the ethylene-vinyl acetate copolymer resin sold under the Registered Trademark Elvax. The present invention contemplates using any deformable material 20 suitable to form a mold of at least some of the user's upper and lower teeth. As discussed more fully below, by forming a mold of the particular user's teeth, device 10 may be customized to fit the particular user.

In one embodiment, deformable material 20 is heated to a temperature of approximately one hundred and fifty degrees Fahrenheit, using a microwave oven or hot water, for example, so as to place deformable material 20 in its deformable state. Upper arch 12, lower arch 14, or both upper arch 12 and lower arch 14 are then inserted into the user's mouth, either separately or together. The user bites down or otherwise presses at least some of the user's teeth into deformable material 20 in order to form a mold of the user's teeth. Deformable material 20 is then allowed to cool and harden or otherwise take a more permanent shape. These steps may be repeated as many times as necessary or desired in order to form a mold of at least some of the user's upper and lower teeth using deformable material 20.

Alternatively, upper arch 12 and lower arch 14 may themselves be formed from a deformable material suitable for dental uses, for example, methyl methacrylate or a polycarbonate resin thermoplastic such as that sold under the Registered Trademark Lexan. Upper arch 12 and lower arch 14 may be customized to fit the user's teeth in the user's home, in the office of a clinical professional, or in any other suitable location. Upper arch 12 and lower arch 14 may be customized to fit the user's teeth before, during, or after the remainder of device 10 is assembled or otherwise coupled to upper arch 12 and lower arch 14. The present invention contemplates using any combination of materials and techniques suitable to form a mold of at least some of the user's upper and lower teeth.

Whether upper arch 12 and lower arch 14 are themselves formed from a deformable material or are constructed so as to include deformable material 20, properly fitting device 10 to the user's teeth increases the safety and effectiveness of device 10 in treating the particular breathing disorder for which device 10 was constructed. The present invention contemplates using the relining methods discussed in copending application Ser. No. 08/621,133, filed Mar. 21, 1996, to further improve the fit between upper and lower arches 12 and 14, respectively, and the user's teeth. Copending application Ser. No. 08/621,133, filed Mar. 21, 1996, is herein incorporated by reference. Furthermore, various securing clasps, for example, C-clasps, ball clasps, and U-Clasps, may be coupled to upper arch 12 and lower arch 14 in order to more fully secure upper arch 12 and lower arch 14 to the user's teeth when device 10 is in use.

Using tensile member 24, lower arch 14 may be adjustably extended forward, relative to upper arch 12. Tensile member 24 has first and second ends 26 and 28, respectively, that are coupled to lower arch 14 using attachments sites 30 and 32, respectively. The length of tensile member 24 is variable and is chosen to suit a particular user or application of device 10. In one embodiment, the locations of attachment sites 30 and 32 on lower arch 14 are also variable. The particular attachment sites 30 and 32 that couple first and second ends 26 and 28, respectively, to lower arch 14 are chosen from among a plurality of available attachment sites 30 and 32. Attachment sites 30 and 32 may include, without limitation, hooks for tying first and second ends 26 and 28 to lower arch 14, holes for force-fitting or gluing first and second ends 26 and 28 into lower arch 14, or any other mechanism for coupling first and second ends 26 and 28, respectively, to lower arch 14.

Adjustor 34 is coupled to upper arch 12 and is coupled to tensile member 24 between first end 26 and second end 28 of tensile member 24. Adjustor 34 may be integral to or separate from upper arch 12. Adjustor 34 may be formed from the same material as upper arch 12 or from a different material than upper arch 12. In one embodiment, adjustor 34 includes a tubular housing that is fixedly attached to upper arch 12. As discussed more fully below in connection with FIGS. 2a-2c, adjustor 34 is used to adjust the position of tensile member 24.

Tensile member 24 can be made to exert a tensile force upon lower arch 14 when device 10 is properly inserted into the user's mouth. The tensile force exerted by tensile member 24 upon lower arch 14 increases when adjustor 34 is appropriately adjusted, thereby pulling lower arch 14 forward, relative to upper arch 12. Similarly, the tensile force exerted by tensile member 24 upon lower arch 14 decreases when adjustor 34 is appropriately adjusted, thereby allowing lower arch 14 to retract, relative to upper arch 12. In this manner, lower arch 14 may be adjustably positioned forwardly, relative to upper arch 12, using adjustor 34. The present invention contemplates any adjustor 34 suitable for adjustably positioning lower arch 14, relative to upper arch 12. The present invention further contemplates two or more tensile members to replace or combine with the functions of tensile member 24.

Support loops 36 and 38 are coupled to upper arch 12 using attachment sites 40 and 42, respectively. In one embodiment, the locations of attachment sites 40 and 42 on upper arch 12 are variable. The particular attachment sites 40 and 42 used to couple support loops 36 and 38, respectively, to upper arch 12 are chosen from among a plurality of available attachment sites 40 and 42. Tensile member 24 contacts and is redirected by support loop 36 along a first loop contact region of tensile member 24 between adjustor 34 and first end 26 of tensile member 24. Similarly, tensile member 24 contacts and is redirected by support loop 38 along a second loop contact region of tensile member 24 between adjustor 34 and second end 28 of tensile member 24.

In combination, support loops 36 and 38 and attachment sites 30 and 32, respectively, define the angle at which tensile member 24 couples to lower arch 14. Therefore, support loops 36 and 38 and attachment sites 30 and 32, respectively, also define the angle from which tensile member 24 exerts a tensile force upon lower arch 14. By varying the relative positions and constructions of support loops 36 and 38 and attachment sites 30 and 32, respectively, the forward and vertical components of the tensile force may be defined according to the particular user or application of device 10. For example, it may be desirable to increase the forward component of the tensile force, relative to the vertical component, such that lower arch 14 is not pulled off of the user's lower teeth when the mouth is opened or the lower jaw is otherwise moved. In addition, due to the configuration of lower arch 14, tensile member 24, and support loops 36 and 38, lower arch 14 may move laterally in response to lateral movements of the lower jaw.

The present invention contemplates any suitable support surfaces to replace or combine with the functions of support loops 36 and 38. The present invention contemplates support loops 36 and 38 coupled to lower arch 14 at variable attachment sites on lower arch 14 instead of, or in addition to, support loops 36 and 38 coupled to upper arch 12. Using any suitable combination of tensile member 24, adjustor 34, support loops 36 and 38, and attachment sites 30 and 32, and 40 and 42, lower arch 14 may be adjusted forwardly, relative to upper arch 12, by exerting a tensile force upon lower arch 14.

Figure 2A:
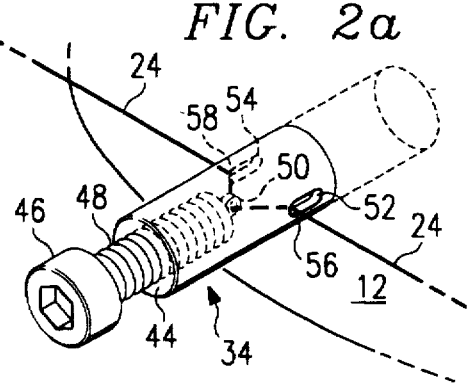
FIGS. 2a–2c illustrate exploded views of adjustors.
Figure 2B:
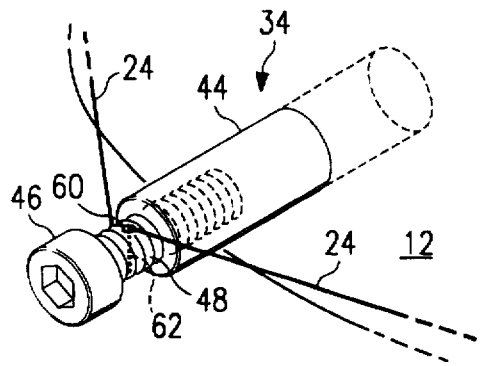
Figure 2C:
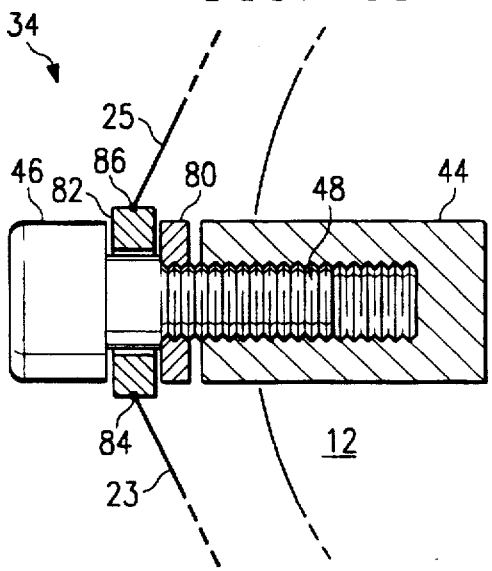

FIGS. 2a-2c illustrate exploded views of adjustors for use in connection with device 10. As shown in FIG. 2a, adjustor 34 includes a housing 44 coupled to upper arch 12 and an adjustment element 46. Housing 44 may be integral to or separate from upper arch 12. Housing 44 may be formed from the same materials as upper arch 12 or from different materials than upper arch 12. Housing 44 may be entirely exterior to upper arch 12 or may lie partially within upper arch 12. In one embodiment, housing 44 is fixedly attached to upper arch 12 by force-fitting, gluing, or otherwise inserting a portion of housing 44 into a hole in the outward surface of upper arch 12. The present invention contemplates forming housing 44 from any suitable material and coupling housing 44 to upper arch 12 in any suitable manner.

In one embodiment, housing 44 is tubular and is threaded along at least a portion of its interior surface. Adjustment element 46 includes a completely or partially threaded shaft 48 that mates with the threads on the interior surface of housing 44. Adjustment element 46 is coupled to tensile member 24 using a hooking element 50 located near the proximal end of adjustment element 46. Tensile member 24 passes through hooking element 50 along a coupling region of tensile member 24. Tensile member 24 is displaced forwardly, relative to upper arch 12, when hooking element 50 is displaced forwardly. The present invention contemplates coupling two or more tensile members to hooking element 50 in order to replace or combine with the functions of tensile member 24. As discussed more fully below, hooking element 50 maintains its rotational orientation, relative to housing 44, when adjustment element 46 is displaced forwardly.

In one embodiment, housing 44 includes slots 52 and 54. Slots 52 and 54 are located between hooking element 50 and support loops 36 and 38, respectively. Tensile member 24 passes through slots 52 and 54. When adjustment element 46 is displaced forwardly, relative to upper arch 12, tensile member 24 is pulled forwardly by hooking element 50. Tensile member 24 contacts and is redirected by support surfaces 56 and 58 along first and second surface contact regions of tensile member 24, respectively. When adjustment element 46 has been displaced forwardly to a sufficient extent, relative to upper arch 12, the friction forces generated at hooking element 50, support surfaces 56 and 58, and support loops 36 and 38 impede or prevent tensile member 24 from moving laterally through hooking element 50. Therefore, lower arch 14 is displaced equally by first end 26 and second end 28 of tensile member 24 when adjustment element 46 is displaced.

In one embodiment, adjustment element 46 is a cap screw that is displaced, relative to upper arch 12, by rotating the cap screw in the appropriate direction. Hooking element 50 is constructed and coupled to adjustment element 46 so as to maintain the rotational orientation of hooking element 50, relative to housing 44, when adjustment element 46 rotates. As a result, the coupling region of tensile member 24 does not twist or otherwise deform as adjustment element 46 is displaced. The present invention contemplates other configurations of housing 44, adjustment element 46, with or without support surfaces 56 and 58, and tensile member 24 suitable to adjustably position lower arch 14 forwardly, relative to upper arch 12, by exerting a tensile force upon lower arch 14.

As shown in FIG. 2b, tensile member 24 may pass through a hole 62 formed through shaft 48 of adjustment element 46. In one embodiment, adjustment element 46 is a cap screw and hole 62 is formed through an unthreaded portion of shaft 48. As discussed above in connection with FIG. 2a, adjustment element 46 may be rotated in an appropriate direction to displace adjustment element 46 forwardly, relative to upper arch 12.

When adjustment element 46 is rotated, tensile member 24 contacts and is redirected by first and second hole support surfaces 60 and 64, respectively, located at opposite ends of hole 62. As adjustment element 46 is further rotated, the portions of tensile member 24 located on either side of hole 62 begin to wrap around shaft 48. As tensile member 24 is wrapped around shaft 48 in response to rotation of adjustment element 46, tensile member 24 pulls lower arch 14 forwardly, relative to upper arch 12. The friction forces generated at hole support surfaces 60 and 64 impede or prevent tensile member 24 from moving laterally through hole 62. Therefore, lower arch 14 is displaced equally by first end 26 and second end 28 of tensile member 24 when adjustment element 46 is rotated. The present invention contemplates two or more tensile members coupled to adjustment element 46 using hole 62 or other attachment mechanism in order to replace or combine with the functions of tensile member 24.

As shown in FIG. 2c, adjustor 34 may include an annular flange 80 that is fixedly coupled to shaft 48 of adjustment element 46. When adjustment element 46 is rotated in an appropriate direction, annular flange 80 is displaced forwardly, relative to upper arch 12, to the same extent as the remainder of adjustment element 46. Annular ring 82 is constructed so as to completely or partially encircle a portion of shaft 48 that is forward of annular flange 80, relative to upper arch 12. Annular ring 82 is coupled to tensile members 23 and 25 using attachment sites 84 and 86, respectively, on annular ring 82. The present invention contemplates any suitable mechanism for coupling tensile members 23 and 25 to annular ring 82. The present invention further contemplates a single tensile member coupled to annular ring 82 to replace of combine with the functions of tensile members 23 and 25.

In one embodiment, shaft 48 of adjustment element 46 is threaded at its distal end, relative to upper arch 12, so as to allow the cap portion of adjustment element 46 to be screwed onto the distal end of adjustment element 46 after annular ring 82 has been seated upon annular flange 80. As a result, annular ring 82 may be constrained to move, if at all, only between the cap portion of adjustment element 46 and annular flange 80. Alternatively, the cap portion of adjustment element 46 may be absent or otherwise removed. In that case, annular ring 82 may be seated upon annular flange 80 and unseated from annular flange 80 when tensile members 23 and 25 allow.

In one embodiment, annular flange 80 and annular ring 82 operate so as to maintain the rotational orientation of annular ring 82, relative to housing 44, when adjustment element 46 rotates. As a result, tensile members 23 and 25 do not twist or otherwise deform as adjustment element 46 is displaced. When annular flange 80 is displaced forwardly in response to rotation of adjustment element 46, annular ring 82 is displaced forwardly to the same extent, relative to upper arch 12. As annular ring 82 is displaced forwardly, tensile members 23 and 25 are pulled forwardly, relative to upper arch 12. As a result, lower arch 14 is displaced forwardly, relative to upper arch 12, and is displaced equally by tensile member 23 and tensile member 25. The present invention contemplates other configurations of housing 44, adjustment element 46, with or without annular flange 80, and annular ring 82 suitable to adjustably position lower arch 14 forwardly, relative to upper arch 12, by exerting a tensile force upon lower arch 14.

As shown in FIG. 3, device 10 may include two or more tensile members to replace or combine with the functions of tensile member 24. In one embodiment, tensile members 92 and 94 are coupled to adjustors 66 and 68, respectively, and may be adjusted independently of one another. Adjustors 66 and 68 are coupled to upper arch 12 using attachment sites 70 and 72, respectively. As discussed above in connection with FIG. 1, the locations of attachment sites 70 and 72 on upper arch 12 are variable. Therefore, adjustors 66 and 68 may be variably positioned according to the particular user or application of device 10. The present invention contemplates adjustors 66 and 68 coupled to lower arch 14 instead of, or in addition to, adjustors 66 and 68 coupled to upper arch 14. For example, adjustors 66 and 68 may be coupled to lower arch 14 using attachment sites 30 and 32, respectively, and tensile members 92 and 94 may be coupled to upper arch 14 using attachment sites 70 and 72, respectively.

Adjustors 66 and 68 may be integral to or separate from upper arch 12. Adjustors 66 and 68 may be formed from the same material as upper arch 12 or from a different material than upper arch 12. As shown in FIG. 4, adjustors 66 and 68 may be constructed in the same manner as adjustor 34 discussed above in connection with FIG. 2b. In one embodiment, a stop 63 is coupled to a first end of tensile member 92 and prevents the first end from passing through hole 90 in shaft 48. The second end of tensile member 92 passes through hole 90 and is coupled to lower arch 14 using a particular attachment site 30.

Similar to the above discussion in connection with FIG. 2b, when adjustment element 46 is rotated, tensile member 92 contacts and is redirected by a hole support surface 65 located at the end of hole 90 that is opposite stop 63. When adjustment element 46 is rotated, tensile member 92 contacts and is redirected by hole support surface 65. As adjustment element 46 is further rotated, the portion of tensile member 92 located outside of hole 90 begins to wrap around shaft 48. As tensile member 92 is wrapped around shaft 48 in response to rotation of adjustment element 46, tensile member 92 pulls lower arch 14 forwardly, relative to upper arch 12.

Together with stop 63, the friction forces generated between tensile member 92, hole support surface 65, and shaft 48 impede or prevent tensile member 92 from moving within hole 90. Adjustors 66 and 68 are independently adjustable, and the above discussion regarding tensile member 92 and adjustor 66 applies equally to the construction and operation of tensile member 94 and adjustor 68. In combination, tensile members 92 and 94 adjustably position lower arch 14 forwardly, relative to upper arch 12, by exerting a tensile force upon lower arch 14.

As shown in FIG. 5, device 10 may include a channel 74 to replace or combine with the functions of adjustor 34 and loop support surfaces 36 and 38. In one embodiment, channel 74 receives tensile member 24 along a contact region of tensile member 24 located between first end 26 and second end 28 of tensile member 24. Channel 74 may be integral to or separate from upper arch 12. For example, channel 74 may be formed through a portion of upper arch 12 or channel 74 may be a separate element coupled to upper arch 12 in some manner. Channel 74 may be formed from the same material as upper arch 12 or from a different material than upper arch 12. The present invention contemplates any channel 74 suitable for receiving a portion of tensile member 24.

In one embodiment, channel 74 is formed using a tubular member coupled to the generally forward and downward surface of upper arch 12. Tensile member 24 passes through channel 74, contacts and is redirected by first and second channel support surfaces 76 and 78, respectively, and is coupled to lower arch 14 using attachment sites 30 and 32.

As discussed above in connection with FIG. 1, the length of tensile member 24 and the locations of attachment sites 30 and 32 on lower arch 14 are variable and may be chosen to suit a particular user or application of device 10.

Although friction forces generated by channel support surfaces 76 and 78 may impede or prevent tensile member 24 from moving within channel 74, the present invention contemplates tensile member 24 moving laterally in response to certain movements of the user's lower jaw. The present invention further contemplates a plurality of tensile members to replace or combine with the functions of tensile member 14. Using any suitable combination of adjustor 34, channel 74, and tensile member 24, lower arch 14 may be adjustably positioned forwardly, relative to upper arch 12, by exerting a tensile force upon lower arch 14.

Although the present invention has been described above in connection with several embodiments, it should be understood that a plethora of changes, substitutions, variations, alterations, transformations, and modifications may be suggested to one skilled in the art, and it is intended that the present invention encumbers such changes, variations, substitutions, alterations, transformations, and modifications as fall within the spirit and scope of the appended claims.

What is claimed is:

1. A device for improving breathing, comprising:
   - an upper arch adapted to receive at least some of a user's upper teeth;
   - a lower arch adapted to receive at least some of the user's lower teeth; and
   - a tensile member coupled to the upper arch and the lower arch, the tensile member operable to exert a pulling force upon the lower arch, wherein the tensile member may be adjusted to pull the lower arch forwardly.

2. The device of claim 1, wherein the tensile member is coupled to the lower arch at ends of the tensile member, the tensile member coupled to the upper arch between the ends.

3. The device of claim 1, further comprising an adjustor coupled to the tensile member and the upper arch, the adjustor operable to adjust the tensile member to pull the lower arch forwardly.

4. The device of claim 3, wherein the adjustor comprises:
   - a housing coupled to the upper arch;
   - an adjustment element coupled to the tensile member and the housing, the adjustment element operable to pull the lower arch forward when the adjustment element is displaced forwardly relative to the housing.

5. The device of claim 3, wherein the adjustor includes a support surface operable to contact the tensile member along a contact region of the tensile member, the adjustor coupled to the tensile member along a coupling region of the tensile member, the contact region located between the coupling region and an end of the tensile member.

6. The device of claim 1, further comprising:
   - an adjustor coupled to the tensile member and the upper arch, the tensile member coupled to the lower arch at ends of the tensile member; and
   - a support surface coupled to the device and contacting the tensile member along a contact region of the tensile member located between the adjustor and one of the ends.

7. The device of claim 6, wherein the location of the support surface is variable.

8. The device of claim 6, wherein the support surface is coupled to the upper arch.

9. The device of claim 1, further comprising:
   - an adjustor coupled to the tensile member and the upper arch, the tensile member coupled to the lower arch at ends of the tensile member;

a first support surface coupled to the upper arch and operable to contact the tensile member along a first contact region of the tensile member located between the adjustor and a particular end of the tensile member; and a second support surface coupled to the lower arch and operable to contact the tensile member along a second contact region of the tensile member located between the first contact region and the particular end of the tensile member.

10. The device of claim 1, wherein the tensile member has first and second ends coupled to the lower arch at first and second attachment sites, respectively, the locations of the first and second attachment sites being variable.

11. A device for improving breathing, comprising:

an upper arch adapted to receive at least some of a user's upper teeth and including a channel;

a lower arch adapted to receive at least some of the user's lower teeth; and a tensile member coupled to the upper arch and the lower arch, the channel slidingly receiving the tensile member, the tensile member operable to exert a pulling force upon the lower arch, wherein the tensile member may be adjusted to pull the lower arch forwardly.

12. The device of claim 11, wherein the channel comprises a tubular member coupled to the upper arch and operable to receive the tensile member.

13. The device of claim 11, wherein the tensile member is coupled to the lower arch at ends of the tensile member, the channel receiving the tensile member along a contact region of the tensile member between the ends.

14. A device for improving breathing, comprising:

an upper arch adapted to receive at least some of a user's upper teeth;

a lower arch adapted to receive at least some of the user's lower teeth; and a plurality of tensile members coupled to the upper arch and the lower arch, wherein at least one of the tensile members may be adjusted to pull the lower arch forwardly.

15. The device of claim 14, further comprising an adjustor coupled to the tensile members and the upper arch, the tensile members coupled to the adjustor at first ends and coupled to the lower arch at second ends, the adjustor operable to adjust the tensile members.

16. The device of claim 14, further comprising a plurality of adjustors, each adjustor coupled to a corresponding tensile member and operable to independently adjust the corresponding tensile member.

17. The device of claim 16, wherein each particular adjustor comprises:

a housing coupled to the upper arch;

an adjustment element coupled to the particular tensile member and the housing, the adjustment element operable to pull the lower arch forward when the adjustment element is displaced forwardly relative to the housing.

18. The device of claim 16, wherein each particular adjustor includes a support surface, the particular tensile member coupled to the adjustor at a first end and coupled to the lower arch at a second end, the support surface operable to contact the particular tensile member along a contact region of the particular tensile member between the first end and the second end.

19. The device of claim 16, further comprising a plurality of attachment sites, each adjustor coupled to the upper arch using a corresponding attachment site, the locations of the attachment sites on the upper arch being variable.

20. The device of claim 14, further comprising a plurality of attachment sites, each tensile member coupled to the lower arch using a corresponding attachment site, the locations of the attachment sites on the lower arch being variable.

* * * * *